United States Patent
Lee et al.

(10) Patent No.: US 6,693,180 B2
(45) Date of Patent: Feb. 17, 2004

(54) COMPOSITE SPONGE WOUND DRESSING MADE OF β-CHITIN AND CHITOSAN AND METHOD FOR PRODUCING THE SAME

(75) Inventors: Jui-Sheng Lee, Tu-Chen (TW); Chun-Yuan Hsu, Tu-Chen (TW); Wei-Hsin Lin, Tu-Chen (TW)

(73) Assignee: China Textile Institute, Taipei Hsien (TW)

( * ) Notice: Subject to any disclaimer, the term of this patent is extended or adjusted under 35 U.S.C. 154(b) by 106 days.

(21) Appl. No.: 10/115,007

(22) Filed: Apr. 4, 2002

(65) Prior Publication Data

US 2003/0190346 A1 Oct. 9, 2003

(51) Int. Cl.$^7$ ................................................ C08B 37/08
(52) U.S. Cl. .......................... 536/20; 536/55; 536/55.1; 536/18.7; 536/123.1; 536/55.3
(58) Field of Search ...................... 514/55, 54; 536/20, 536/55.1, 18.7, 17.2, 55, 123.1, 55.3

(56) References Cited

FOREIGN PATENT DOCUMENTS

EP     0 477 979 A2 *  9/1991

OTHER PUBLICATIONS

Ogasawara et al., Chemistry of Materials (2000), 12 (10), 2835–2837; (abstract sent).*

* cited by examiner

*Primary Examiner*—Samuel Barts
*Assistant Examiner*—Michael C. Henry
(74) *Attorney, Agent, or Firm*—Troxell Law Office PLLC

(57) ABSTRACT

The present invention relates to a composite sponge wound dressing and method for producing the same. Chitosan and β-Chitin is mixed in a specific ratio for forming the sponge for wound repairing. Particularly, when said ratio is between 0.1~1, the composite sponge wound dressing has a better absorption and tensile strength.

10 Claims, 5 Drawing Sheets

TABLE 1

| Composite Sponge with Different Ratio of $\beta$-Chitin and Chitosan | Original Weight (Unit : g) | After Immersing (Unit : g) | Absorbing Ability Value |
|---|---|---|---|
| Chitin 8g (N/A) | 0.101 | 4.756 | 46 |
| Chitin 8g +Chitosan 1g (0.125) | 0.122 | 2.567 | 20 |
| Chitin 8g +Chitosan 2g (0.25) | 0.110 | 1.873 | 17 |
| Chitin 8g +Chitosan 4g (0.5) | 0.070 | 0.778 | 10 |
| Chitin 8g +Chitosan 8g (1) | 0.108 | 0.810 | 6.5 |

TABLE 2

| Composite Sponge with Different Ratio of β-Chitin and Chitosan | Loading Weight (dry) (Unit : kg) | Tensile Strength (dry) (Unit : kg/cm$^2$) | Loading Weight (wet) (Unit : kg) | Tensile Strength (wet) (Unit : kg/cm$^2$) |
|---|---|---|---|---|
| Chitin 8g (N/A) | 0.460 | 0.046 | 0.060 | 0.006 |
| Chitin 8g +Chitosan 1g (0.125) | 1.230 | 0.123 | 0.860 | 0.086 |
| Chitin 8g +Chitosan 2g (0.25) | 1.740 | 0.174 | 1.100 | 0.110 |
| Chitin 8g +Chitosan 4g (0.5) | 2.300 | 0.230 | 1.230 | 0.123 |
| Chitin 8g +Chitosan 8g (1) | 2.840 | 0.284 | 1.740 | 0.174 |

TABLE 3

| Time \ Sample | Control Group (Repairing%) | Experiment Group (Repairing%) |
|---|---|---|
| 3 days | -16.67 ±0 | 2.07 ±9.94 |
| 7 days | -7.07 ±6.80 | 20.15 ±3.59 |
| 14 days | 33.04 ±11.36 | 70.22 ±8.66 |
| 21 days | 47.67 ±11.26 | 83.26 ±8.32 |

COMPOSITE SPONGE WOUND DRESSING MADE OF β-CHITIN AND CHITOSAN AND METHOD FOR PRODUCING THE SAME

FIELD OF THE INVENTION

The invention herein relates to a wound dressing, particularly, relates to a composite sponge wound dressing made of β-Chitin and Chitosan for accelerating wound repair.

BACKGROUND OF THE INVENTION

Normally, wound dressing needs to provide some basic physical and biological function, such as avoiding water or liquid loss, human skin-like with flexibility, gas permeation, water vapor flux, absorbing wound exudate, mechanical strength, anti-bacterial or sterilization without causing wound aggravation, adherence to wound, non-toxicity, improvement of epithelization, analgesia, hemostasis, and non-irritant etc. Therefore, there were varies of wound dressing being developed for satisfying the aforementioned requirements.

Chitin is a nature cellulose-like macromolecule extracted from crab or shrimp waste shells. Prudden et al. has developed the research of the wound repair since 1970, and the wound dressing has been commercialized as medical product named "bas-Chitin W", produced by UNITIKA, Japan, and its clinical manifestation was good, as disclosed in Nishinihon Journal of Dermatology Fukuoka Japan, vol. 54, no. 5, pp. 998–1008, 1992. There were many different wound dressing, such as non-woven and porous composition and membrane, each of them was applied in different wound respectively, and its clinical manifestation was good (such as "bedsore treatment" disclosed in Nishinihon Journal of Dermatology Fukuoka Japan, vol. 52, no. 2, pp. 761–764, 1990; "wound dressing experiment" disclosed in Nishinihon Journal of Dermatology Fukuoka Japan, vol. 50 no. 4, pp. 712–724, 1998; "incision treatment" disclosed in Nishinihon Journal of Dermatology Fukuoka Japan, vol. 48, no. 6, pp. 1119–1122). However, the Chitin extracted from crab or shrimp shells is α-Chitin, and its energy of stereo structure between the molecules is very stable, therefore, it has a stronger molecular structure, which needs some special organic solvent to dissolve (like LiCL/N,N-dimethyl acetamide), as a result, it is limited in developing its application, and furthermore, the solvent may cause problems of safety issue and environment pollution.

In general, according to the different structure of molecules, there are three Chitins: α-Chitin (such as extracted from crab or shrimp shells), β-Chitin (such as extracted from the cuttlefish cartilage), and γ-Chitin. The energy of stereo structure between the molecules of α-Chitin is the most stable, therefore, it has the strongest molecular structure, which needs some special organic solvent to dissolve (such as LiCL/N,N-dimethyl acetamide), as a result, it is limited in developing its application, and furthermore, the solvent may cause problems of safety issue and environment pollution. Due to the energy of stereo structure between the molecules of β-Chitin is not very stable, it can absorb liquid, and can be formed in short staple by high speed blending. The Japan Patent Publication Number 07-47113, "Therapeutic Agent", discloses porous β-Chitin producing by high speed blending and freeze-drying method, and also, the Japan Patent publication number 03-41131, "Production of porous Chitin molding", uses the same method to produce the porous β-Chitin. However, the β-Chitin produced in accordance with the above method has lower tensile strength (dry/wet). The heaviest loading is 0.46 kg and tensile strength is 0.046 kg/cm$^2$ (dry), and 0.06 kg loading and 0.006 kg/cm$^2$ tensile strength (wet). Being a wound dressing, it may cause breakage when absorbing the wound exudate, so it is inconvenience for surgery operation.

Chitosan is a macromolecules production through deacetylation from Chitin. The U.S. Pat. No. 4,532,134, "method of achieving hemostasis, inhibiting fibroplasias, and promoting tissue regeneration in a tissue wound", indicates that the medical property of Chitosan includes hemostasis, hindered of growth of fibroblast, and improving tissue regeneration. Besides, Japan Patent Publication Number 08-224293, "Multilayered body for treating wound", also indicates that the medical property of Chitosan includes activating macrophage and leukocyte, anti-bacterial, and further preventing wound suppurated. Therefore, the present invention provides a composite sponge wound dressing made of β-Chitin and Chitosan, which not only can absorb liquid, but also can keep good tensile strength.

SUMMERY OF THE INVENTION

This invention provides a composite sponge wound dressing made of β-Chitin and Chitosan and method for producing the same. Putting β-Chitin into D.I. water, and then blending them with high speed until forming a hydrogel β-Chitin, at the same time, filtering Chitosan by solving thereof, next, mixing said hydrogel β-Chitin and said Chitosan to form a sponge by freeze-drying. Immersing said sponge in an alkaline liquid for forming salt by neutralization, after salt formed, clean said sponge to neutral. At last, said sponge is cleaned repeatedly with D.I. Water and formed a composite sponge wound dressing made of β-Chitin and Chitosan by vacuum drying. In the preferred embodiment, when the mixing ratio of Chitosan and β-Chitin being between 0.1~1, the composite sponge wound dressing has a better absorption and tensile strength.

BRIEF DESCRIPTION OF THE DRAWINGS

The present invention will be better understood from the following detailed description of preferred embodiments of the invention, taken in conjunction with the accompanying drawings, in which TABLE 1. is an absorption test of the present invention;

TABLE 2. is a tensile strength test of the present invention;

Figure 1:
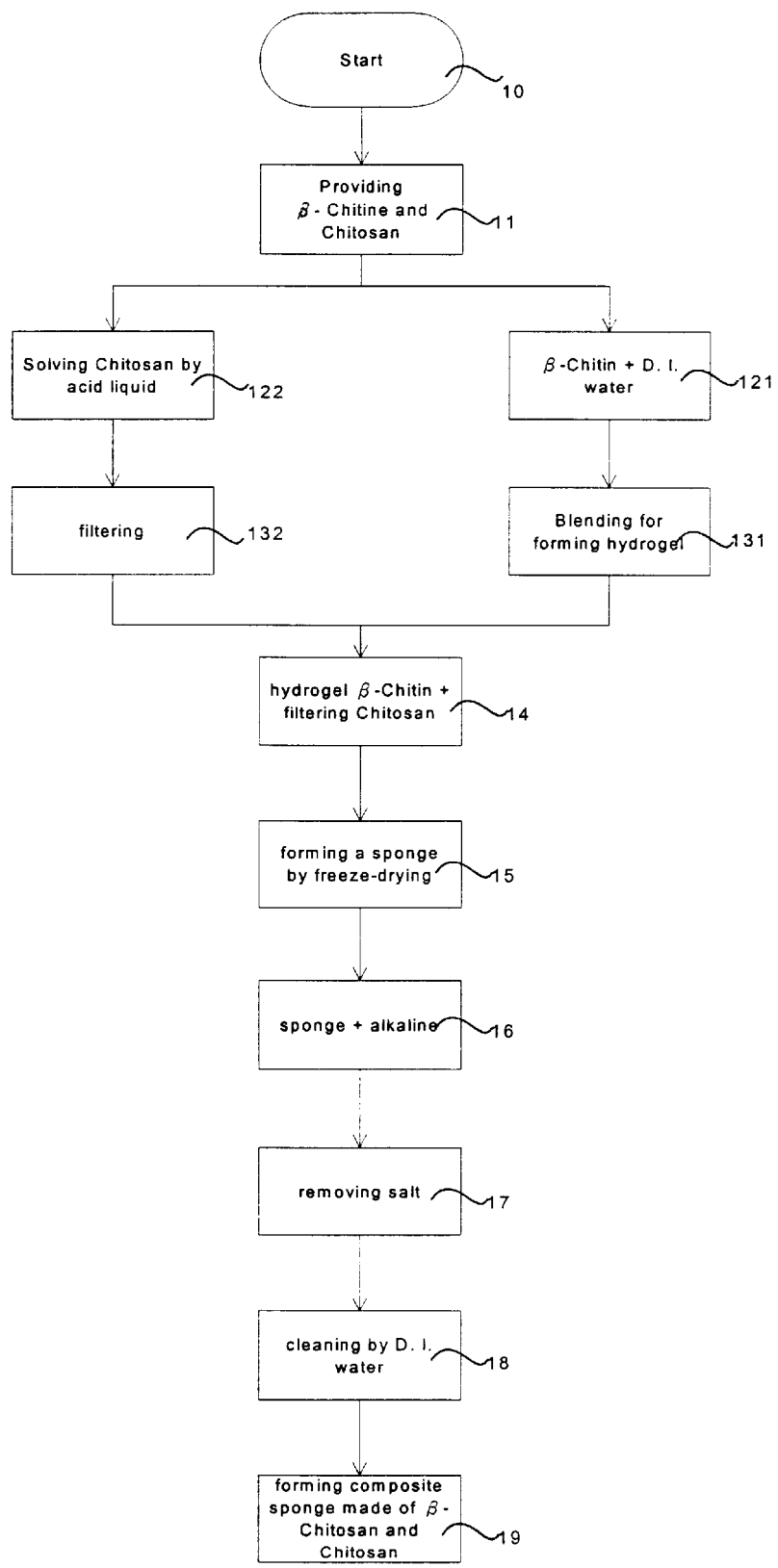

TABLE 3. is a wound-repairing comparison of the present invention;

FIG. 1. is a flow chart for describing the procedure of this invention; and

Figure 2:
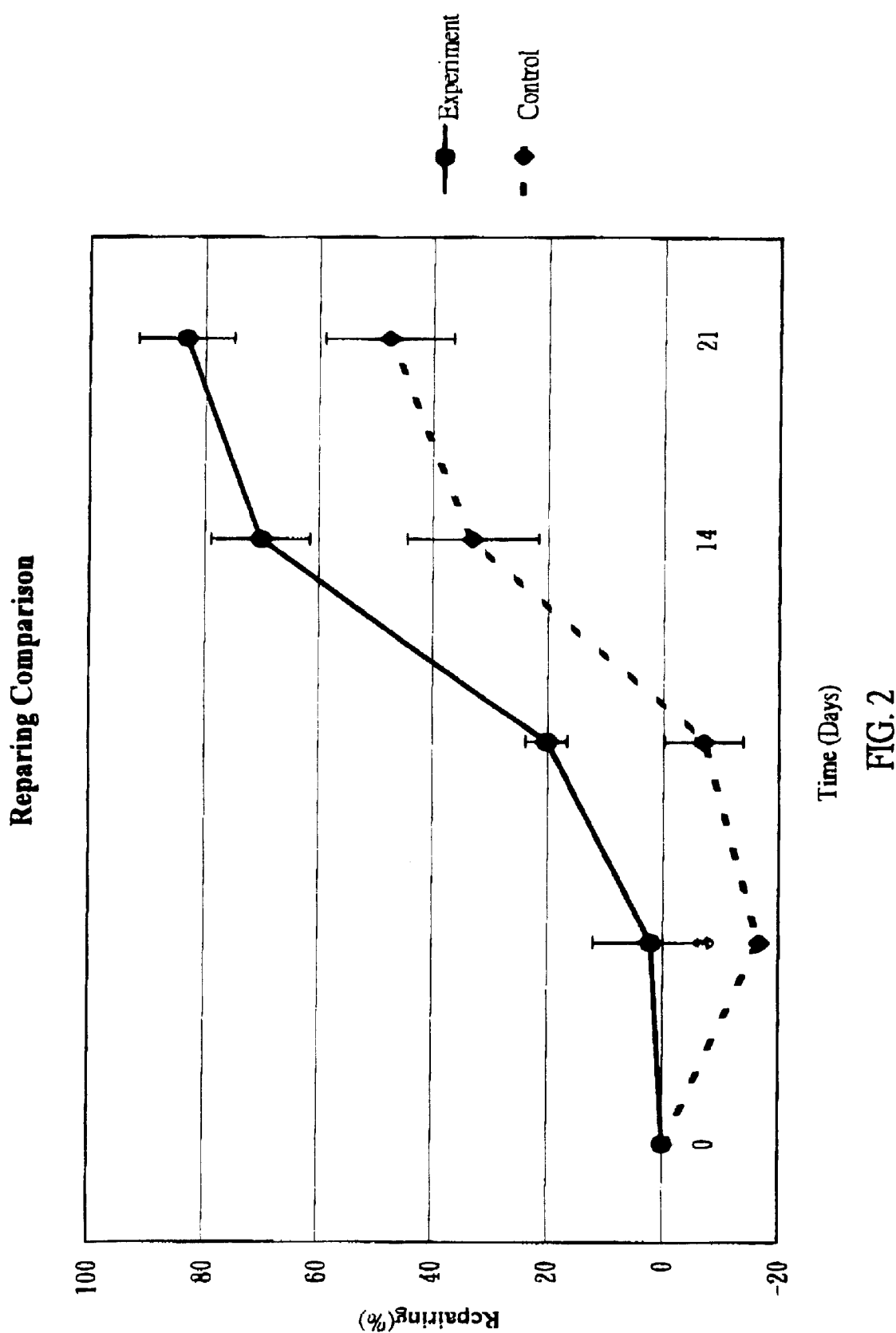

FIG. 2. is a comparing figure in accordance with the TABLE 3.

DESCRIPTION OF THE PREFERRED EMBODIMENTS

The following descriptions of the preferred embodiments are provided to understand the features of the present invention.

The present invention provides a composite sponge wound dressing made of β-Chitin and Chitosan and method for producing the same. Please referring to the flow chart of FIG. 1, which starts from step 10, then step 11 is providing a β-Chitin and a Chitosan. Next, step 121 and step 122 can be processed synchronically; step 121 is putting said β-Chitin in deionized water (D.I. Water) for suspending thereof, then blending said β-Chitin in high speed (such as more than 12,000 rpm) for forming a hydrogel β-Chitin in step 131, in the preferred embodiment, said β-Chitin is a short staple β-Chitin; and step 122 is solving said Chitosan by an acid liquid, in the preferred embodiment, said Chitosan is a membrane Chitosan, furthermore, said acid liquid is a 2% acetic acid, then filtering said Chitosan in step 132. Next, step 14 is mixing said hydrogel β-Chitin from step 131 and said Chitosan from step 132. Particularly, said Chitosan and said β-Chitin is mixing with a specific ratio between 0.1~1 for a better absorption and tensile strength, furthermore, in the preferred embodiment, said ratio is between 0.125~0.5. In step 15, a sponge is formed by freeze-drying. Chitosan is very easy to be solved in acid, therefore, in step 16, said sponge is immersed in an alkaline liquid for forming salt by neutralization, in a preferred embodiment, said alkaline liquid is a 5% sodium hydroxide (NaOH) liquor. Next coming to step 17, cleaning and removing said salt with water until said sponge becoming neutral. Due to this invention may be used for wound repairing, in step 18, it is important to clean said composite sponge with D.I. Water repeatedly for ensuring said sponge is cleaned. And at last, the process comes to step 19: producing a composite sponge wound dressing made of β-Chitin and Chitosan by vacuum drying. In the preferred embodiment, a protection dressing is provided for covering said composite sponge wound dressing for wound repairing, furthermore, wherein said protection dressing is selected from a group of PU film, bandage, non-woven, fabric, paper, and tape.

Therefore, the present invention provides a composite sponge wound dressing made of β-Chitin and Chitosan, which comprises a specific ratio of Chitosan and β-Chitin for wound repairing. In the preferred embodiment, said β-Chitin is a short staple β-Chitin, and said Chitosan is a membrane Chitosan. From the test result, it can be known that when the ratio of Chitosan and β-Chitin is between 0.1~1, the composite sponge wound dressing has a better absorption and tensile strength, in the preferred embodiment, the ratio is between 0.125~0.5. Please referring to TABLE 1, cutting a composite sponge wound dressing produced in accordance with the above method of the present invention with a specific ratio of Chitosan and β-Chitin in 2 cm×5 cm, then immersing it into saline water three minutes, and after wiping its surface with a dry paper. As a result, the TABLE 1 shows the absorbing ability of the present invention; wherein the first column of TABLE 1 is different ratio of Chitosan and β-Chitin produced in accordance with the aforementioned method of this invention; the second column of TABLE 1 is the original weight of the composite sponge (before immersing); the third column is the weight after immersing into saline water; and the forth column is the absorbing ability value. The equation of the absorbing ability is based on:

$$\frac{\text{(third column)} - \text{(second column)}}{\text{(second column)}}$$

From the TABLE 1, the composite sponge with β-Chitin (8 g) has the best absorption; it is 46 times than the original weight. When mixing with the Chitosan, its absorption is decreasing, however, its tensile strength is increasing (referring to the TABLE 2). The present invention may be tested by a universal testing machine (Model: HT-8504), and the result is showing in TABLE 2. Every composite sponge with different ratio of Chitosan and β-Chitin was cut into 2 cm×5 cm and immersed into saline water. Then, they were pulled with speed in 50 mm/min separately for testing thereof. From the TABLE 2, it has the worst loading and tensile strength, which are 0.46 kg and 0.046 kg/cm$^2$ respectively. After mixing with Chitosan, the loading and tensile strength is increasing.

Thus, the preferred ratio of Chitosan and β-Chitin is between 0.1~1 for a better absorption and tensile strength, in the preferred embodiment, the ration is between 0.125~0.5. Therefore, when the ratio is between 0.125~0.5, the loading strength is between 1.203 kg~2.840 kg (dry, before immersing), and the tensile strength is between 0.123 kg/cm$^2$~0.284 kg/cm$^2$ (dry); after immersing, the loading strength is between 0.86kg~1.740kg (wet), and the tensile strength is between 0.086 kg/cm$^2$~0.174 kg/cm$^2$ (wet). When the ratio of Chitosan and β-Chitin is bigger than 1, it has a worse absorption, thus, it is improperly used for wound repairing since it may irritate wound. In addition, when the ratio is smaller than 0.06, it has a worse tensile strength, thus, it is improperly used for surgery operation since it is easy to be broken particularly after absorbing the wound exudate. Consequently, when the ratio of Chitosan and β-Chitin is between 0.1~1, it has a better absorption and tensile strength, furthermore, the best ratio is between 0.125~0.5.

This invention comprises a composite sponge wound dressing made of β-Chitin for tissue regeneration and Chitosan for preventing wound suppurated. Besides, this invention also takes the advantage of a better absorption and tensile strength, thus, it can accurate the wound repairing for healing.

In Vitro test, according to the specification of ASTM F813-83 for processing the test of cell toxicity of implant, it is non-toxic after testing with L929 mouse fibroblast.

In Vivo test, three SD-rats (male Spague-Dawley rats with 250 mg~300 mg weight) were provided as experiment group. After anesthetizing by ether, the experiment rats was shaved and disinfected by 10% agueous betadine and 70% alcohol, then they were cut by a surgery knife for forming a wound with 3 cm×3 cm area and depth in panniculus carnosis. After operation, the composite sponge wound dressing made of β-Chitin and Chitosan provided by the present invention covered the wound, then a protection dressing (such as Teggaderm (3M)) was provided to cover said composite sponge, next, fixed with a self-adherence elastic bandage (3M); wherein the protection dressing is selected from the group of PU film, bandage, non-woven, fabric, paper, and tape. In the contrast, another three SD-rats were provided as control group. After the same operation described as above; general iodine tincture covered with swap was used to cover the control group rats for healing. Please referring to the TABLE 3 of wound-repairing comparison, it shows three control group rats and three experiment group rats repairing status. During 21 days observation, the repairing area of the experiment group rats was within 2.07±9.94% (every rat was repaired within this area range) on the third day of the observation, and until the 21$^{st}$ day of the observation, it was within 83.26±8.32%. Referring to the comparison, the repairing area of the control group rats was within −16.67±0% (every rat was repaired within this area range) on the third day of the observation, and until the 21$^{st}$ day, it was within 47.67±11.26%. Obviously, the experiment group rats were repaired much faster than the control group, especially, on the 21$^{st}$ day, the repairing area of the experiment group rats is twice than the control group. In addition, there was almost no purulent wound caused in the experiment group rats while operation was finished, and the control group rats was repaired within −16.67±0% area. On the 7$^{th}$ day of the observation, the repairing area of the experiment group rats (20.15±3.59%) is absolutely better than the control group (still had purulent wound with repairing area of −7.07±6.8%). Furthermore, because the present invention is biodegradable, the wound won't be aggravated by the protection dressing again if it was left in the skin.

Referring to the FIG. 2, the X-axis shows the time after operation (observation days), and the Y-axis shows the repairing percentage; the experiment group is much higher than the control group (dot line) in Y-axis, which means that after the operation the repairing area of the experiment rats is much better than the control group.

Therefore the present invention is providing a composite sponge wound dressing made of β-Chitin and Chitosan for preventing suppurated and wound aggravation. Furthermore, this invention is providing a composite sponge wound dressing made of β-Chitin and Chitosan for anti-bacterial or sterilization, adherence to wound, non-toxity, improving epithelization, analgesia, hemostasis, and non-irritant etc. Due to the specific mixing ratio of Chitosan and β-Chitin, this invention is providing a composite sponge wound dressing for avoiding water or liquid loss, human skin-like with flexibility, gas permeation, water vapor flux, absorbing wound exudate, and tensile strength for healing wound.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

What is claimed is:

1. A method for producing composite sponge wound dressing made of β-Chitin and Chitosan, which comprises the steps of:
   a.) providing a β-Chitin and a Chitosan;
   b.) putting said β-Chitin in deionized water (D.I. Water);
   c.) blending said β-Chitin in high speed for forming a hydrogel β-Chitin;
   d.) solving said Chitosan by an acid liquid;
   e.) filtering said Chitosan;
   f.) mixing said hydrogel β-Chitin from step c and said Chitosan from step e;
   g.) forming a sponge by freeze-drying;
   h.) immersing said sponge in an alkaline liquid for forming salt by neutralization;
   i.) cleaning and removing said salt with water until said sponge becoming neutral;
   j.) cleaning said sponge with D.I. Water repeatedly; and
   k.) producing a composite sponge wound dressing made of β-Chitin and Chitosan by vacuum drying.

2. The method of claim 1, wherein the sequence of the steps b, c and steps d, e is synchronizing.

3. The method of claim 1, the step f mixing said Chitosan and said hydrogel β-Chitin further accords with a specific ratio of Chitosan and β-Chitin, wherein said ratio is between 0.1~1.

4. The method of claim 3, wherein said ratio is between 0.125~0.5.

5. The method of claim 1, wherein said β-Chitin is short staple β-Chitin.

6. The method of claim 1, wherein said Chitosan is membrane Chitosan.

7. The method of claim 1, wherein said acid liquid is 2% acetic acid.

8. The method of claim 1, wherein said alkaline liquid is 5% sodium hydroxide (NaOH) liquor.

9. The method of claim 1, after forming said composite sponge wound dressing made of β-Chitin and Chitosan, further comprises the step of covering said composite sponge wound dressing with a protection dressing for wound repairing.

10. The method of claim 9, wherein said protection dressing is selected from a group of PU film, bandage, non-woven, fabric, paper, and tape.

* * * * *